(12) United States Patent
Shimono et al.

(10) Patent No.: US 12,402,864 B2
(45) Date of Patent: Sep. 2, 2025

(54) ULTRASOUND DIAGNOSTIC APPARATUS

(71) Applicant: FUJIFILM Healthcare Corporation, Kashiwa (JP)

(72) Inventors: Takehiro Shimono, Chiba (JP); Takahide Terada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/429,837

(22) Filed: Feb. 1, 2024

(65) Prior Publication Data

US 2024/0299013 A1 Sep. 12, 2024

(30) Foreign Application Priority Data

Mar. 9, 2023 (JP) .................. 2023-036277

(51) Int. Cl.
*A61B 8/00* (2006.01)
*G01S 7/52* (2006.01)
(52) U.S. Cl.
CPC ............ *A61B 8/54* (2013.01); *G01S 7/52028* (2013.01); *G01S 7/52031* (2013.01)
(58) Field of Classification Search
CPC ............................... A61B 8/54; A61B 8/5207
See application file for complete search history.

(56) References Cited

U.S. PATENT DOCUMENTS

| 4,016,750 A  * | 4/1977 | Green ................. G01S 15/8954 |
| | | 73/620 |
| 2008/0221449 A1 | 9/2008 | Sato |
| 2010/0207489 A1 * | 8/2010 | Huang ................. B81C 1/00182 |
| | | 29/25.35 |
| 2018/0116631 A1 * | 5/2018 | Taniguchi ............ A61B 8/5215 |
| 2020/0138410 A1 * | 5/2020 | Kawabata .............. A61B 8/488 |

FOREIGN PATENT DOCUMENTS

JP 2008/212542 A 9/2008

* cited by examiner

*Primary Examiner* — Jason M Ip
(74) *Attorney, Agent, or Firm* — Paul Teng

(57) ABSTRACT

A passband characteristic of a band pass filter is adapted to an examinee while a texture of an ultrasound image is maintained or is not significantly changed. A passband characteristic of a BPF is dynamically changed in accordance with a depth of an observation point (reception focus). The passband characteristic includes convex forms, and the convex forms have peaks as highest points in a gain axis direction and have widths in a frequency axis direction. A peak position is relatively changed with respect to the width while an upper limit and a lower limit of the width are substantially maintained. Accordingly, the convex forms are biased to a low-frequency side or a high-frequency side.

6 Claims, 6 Drawing Sheets

ULTRASOUND DIAGNOSTIC APPARATUS

CROSS-REFERENCE TO RELATED APPLICATION

The present application claims priority from Japanese patent application 2023-036277 filed with the Japanese Patent Office on Mar. 9, 2023, the content of which is hereby incorporated by reference into this application.

BACKGROUND OF THE INVENTION

1. Field of the Invention

The present disclosure relates to an ultrasound diagnostic apparatus, and particularly relates to control of a passband characteristic of a band pass filter that processes a reception signal.

2. Description of the Related Art

An ultrasound diagnostic apparatus is used in an ultrasound examination of an examinee. The ultrasound diagnostic apparatus includes an ultrasound probe, a transmission unit, a reception unit, a band pass filter, an image formation unit, and the like (see, for example, JP2008-212542A). The ultrasound radiated in a living body and a reflected wave generated in the living body are attenuated as the reflected wave travels in the living body. In this case, a high-frequency component is more significantly attenuated than a low-frequency component. This phenomenon is referred to as frequency-dependent attenuation. The band pass filter is a band pass filter that removes unnecessary components in the reception signal in accordance with the frequency-dependent attenuation.

In the ultrasound diagnostic apparatus, in general, the passband characteristic of the band pass filter is dynamically changed in accordance with an increase in a depth of an observation point (reception focus). Specifically, as the depth of the observation point is increased, a center of the passband characteristic is shifted to the low-frequency side, and a width of the passband characteristic is reduced. The change in the width of the passband characteristic is accompanied by a change in an upper limit (in some cases, an upper limit and a lower limit) of a passband.

In the related art, a form of the passband characteristic is basically maintained in a case in which the passband characteristic is changed. That is, a position and a width of a function exhibiting the passband characteristic are changed in a frequency axis direction while a similar shape is maintained. It should be noted that JP2008-212542A does not describe a modification of the passband characteristic.

SUMMARY OF THE INVENTION

The propagation (specifically, an attenuation characteristic) of the ultrasound in the examinee is changed in accordance with a physique (particularly, an amount of fat) of the examinee. Therefore, it is desired to adapt the passband characteristic of the band pass filter to a tissue property for each observation point depth. In this case, in a case in which only the upper limit (in some cases, the upper limit and the lower limit) of the passband characteristic is shifted, there is a concern that a texture of an ultrasound image is significantly changed and a user feels uncomfortable.

An object of the present disclosure is to adapt the passband characteristic of the band pass filter to the examinee while the texture of the ultrasound image is maintained or is not significantly changed. Alternatively, an object of the present disclosure is to provide a new method of changing the passband characteristic of the band pass filter.

The present disclosure relates to an ultrasound diagnostic apparatus including: an ultrasound oscillator (a transducer) that transmits ultrasound to an inside of an examinee and receives a reflected wave from the inside of the examinee; a band pass filter through which a reception signal output from the ultrasound oscillator passes; an image formation unit (a former) that forms an ultrasound image based on the reception signal output from the band pass filter; and a controller that changes a passband characteristic of the band pass filter in accordance with an increase in an observation point depth in the examinee, in which the passband characteristic has a convex form, and the convex form has a peak as a highest point in a gain axis direction, and a width in a frequency axis direction, and the controller changes a peak position with respect to the width in accordance with the examinee at at least one observation point depth.

According to the present disclosure, it is possible to adapt the passband characteristic of the band pass filter to the examinee while the texture of the ultrasound image is maintained or is not significantly changed. Alternatively, according to the present disclosure, it is possible to provide a new method of changing the passband characteristic of the band pass filter.

DESCRIPTION OF THE PREFERRED EMBODIMENTS

Figure 1:
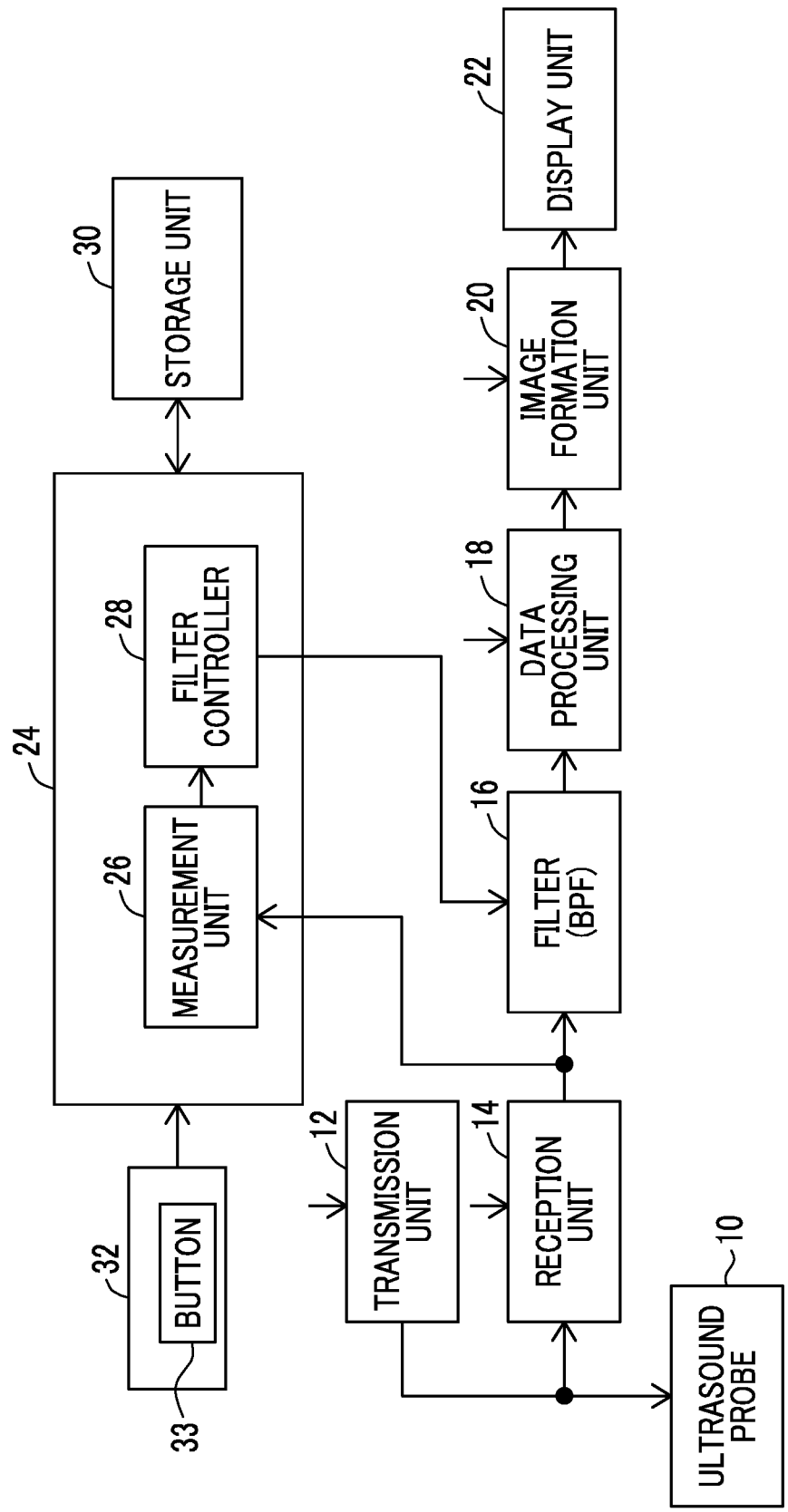
FIG. 1 is a block diagram showing a configuration example of an ultrasound diagnostic apparatus according to an embodiment.

Hereinafter, an embodiment will be described with reference to the accompanying drawings.

(1) Outline of Embodiment

An ultrasound diagnostic apparatus according to an embodiment includes an ultrasound oscillator, a band pass filter, an image formation unit, and a controller. The ultrasound oscillator transmits ultrasound to an inside of an examinee and receives a reflected wave from the inside of the examinee. A reception signal output from the ultrasound oscillator passes through a band pass filter. The image formation unit forms an ultrasound image based on the reception signal output from the band pass filter. The controller changes a passband characteristic of the band pass filter in accordance with an increase in an observation point depth in the examinee. In the embodiment, the passband characteristic has a convex form, and the convex form has a peak as a highest point in a gain axis direction, and a width in a frequency axis direction. The controller changes a peak position with respect to a width in accordance with the examinee at at least one observation point depth.

The configuration described above changes a degree of biasing of the convex form to change the passband characteristic. Therefore, it is possible to change a ratio between a high-frequency component amount and a low-frequency component amount while a significant change in a texture of the ultrasound image is avoided. The width of the convex form may be changed as the peak position is changed, but it is desirable that the width of the convex form is maintained as the peak position is changed.

In the embodiment, the controller dynamically changes the peak position in accordance with the increase in the observation point depth, in accordance with the examinee. For example, in a case of a slightly slim examinee or an examinee who has a small amount of fat, the peak position is shifted to a high-frequency side at each observation point depth. On the other hand, in a case of a slightly fat examinee or an examinee who has a large amount of fat, the peak position is shifted to a low-frequency side at each observation point depth. In the embodiment, the width in the frequency axis direction is a width at constant gain determined with the peak as a reference. For example, the constant gain may be determined in the design of the band pass filter.

In the embodiment, an upper limit and a lower limit of the width are substantially maintained in a case in which the peak position is changed with respect to the width. For example, at each observation point depth, the width (specifically, the upper limit and the lower limit) of the passband characteristic is decided in accordance with a reference attenuation characteristic. The width is fixed, and then the peak position is changed to the low-frequency side or the high-frequency side in accordance with the examinee. The convex form is deformed while being biased to the low-frequency side as the peak position is changed to the low-frequency side. The convex form is deformed while being biased to the high-frequency side as the peak position is changed to the high-frequency side.

In the embodiment, the controller acquires an actual measurement attenuation characteristic based on the reception signal output from the ultrasound oscillator, and decides the peak position with respect to the width based on the actual measurement attenuation characteristic. With this configuration, the passband characteristic is changed based on an actual tissue property of the examinee.

In the embodiment, the controller compares the actual measurement attenuation characteristic with the reference attenuation characteristic, and decides the peak position with respect to the width based on a result of the comparison. The reference attenuation characteristic is registered in advance in the ultrasound diagnostic apparatus. A plurality of reference attenuation characteristics corresponding to a plurality of ultrasound probes, a plurality of reference attenuation characteristics corresponding to a plurality of transmission frequencies, or a plurality of reference attenuation characteristics corresponding to a plurality of examinee types may be registered in advance. The basic reference attenuation characteristic may be corrected in accordance with the examinee, and then the corrected reference attenuation characteristic may be used.

In the embodiment, the ultrasound diagnostic apparatus sequentially executes a preparation step and an examination step. In the preparation step, the actual measurement attenuation characteristic is acquired based on a first reception signal output from the ultrasound oscillator. In the examination step, the passband characteristic of the band pass filter through which a second reception signal output from the ultrasound oscillator passes is changed based on the actual measurement attenuation characteristic.

(2) Details of Embodiment

FIG. 1 shows the ultrasound diagnostic apparatus according to the embodiment. The ultrasound diagnostic apparatus is installed in a medical institution or the like, and is used for an ultrasound examination of the examinee.

An ultrasound probe 10 includes the ultrasound oscillator, and more specifically, includes an oscillation element array (a transducer element array) consisting of a plurality of ultrasound oscillation elements. An ultrasound beam is formed by the oscillation element array, and the electronic scanning with the ultrasound beam is performed. Accordingly, a beam scanning surface is formed in the examinee. The beam scanning surface is a two-dimensional echo data incorporation region. As an electronic scanning method, an electronic linear scanning method, an electronic sector scanning method, or the like is known. A two-dimensional oscillation element array may be provided in the ultrasound probe 10.

A transmission unit 12 is an electronic circuit that functions as a transmission beam former. In the transmission, the transmission unit 12 supplies a plurality of transmission signals in parallel to the oscillation element array. As a result, a transmission beam is formed. A reception unit 14 is an electronic circuit that functions as a reception beam former. In the reception, the reception unit 14 applies phasing addition to a plurality of reception signals output in parallel from the oscillation element array. Accordingly, reception beam data (reception signal after the phasing addition) is generated. The reception unit 14 includes a plurality of amplifiers, a plurality of A/D converters, a plurality of delays, an adder, and the like.

With repetition of the electronic scanning of the ultrasound beam, a reception frame data sequence is output from the reception unit 14. The reception frame data sequence is composed of a plurality of frame data arranged on a time axis. Each reception frame data is composed of a plurality of reception beam data arranged in an electronic scanning direction. Each reception beam data is composed of a plurality of echo data arranged in a depth direction.

The series of reception beam data constituting the frame data sequence are sequentially input to a filter 16 provided in a later stage of the reception unit 14. The filter 16 is a band pass filter (BPF), extracts effective signal components, and removes unnecessary signal components in accordance with frequency-dependent attenuation of the ultrasound in a living tissue. The filter 16 is also referred to as a reception dynamic filter. In reality, the filter 16 is an FIR type filter or an IIR type filter, and a plurality of filter coefficient sequences corresponding to a plurality of observation point depths are given to the filter 16. The passband characteristic of the filter 16 is defined by an individual filter coefficient sequence.

A data processing unit 18 processes each reception beam data output from the filter 16. The data processing unit 18 includes an envelope detector, a logarithmic converter, and the like.

The image formation unit 20 is an electronic circuit that generates a display frame data sequence based on the input reception frame data sequence. The image formation unit 20 includes, for example, a digital scan converter (DSC). The DSC has a coordinate transformation function, a pixel interpolation function, and the like. The display frame data sequence is, for example, a B-mode tomographic image as a moving image. The image formation unit 20 may form another ultrasound image. Examples of the other ultrasound image include a blood flow image.

The ultrasound image is displayed on a display unit 22. The display unit 22 is configured with, for example, an organic EL display device or a liquid crystal display device. For example, the filter 16, the data processing unit 18, and the image formation unit 20 can be configured with a single processor or a plurality of processors.

A calculation controller 24 has various calculation functions and various control functions. The calculation controller 24 is configured with, for example, a CPU that executes a program. The CPU may function as the filter 16, the data processing unit 18, and the image formation unit 20.

The calculation controller 24 according to the embodiment includes a measurement unit 26 and a filter controller 28. The measurement unit 26 functions in the preparation step, and measures the actual measurement attenuation characteristic based on one or the plurality of reception beam data (that is, the reception signal). In other words, the measurement unit 26 acquires the actual measurement attenuation characteristic. The actual measurement attenuation characteristic represents the tissue property of the examinee, and represents an ultrasound attenuation degree or an ultrasound attenuation coefficient for each observation point depth.

The filter controller 28 controls an operation of the filter 16. Specifically, the filter controller 28 calculates the filter coefficient sequence for each observation point depth by comparing the actual measurement attenuation characteristic acquired as described above with the reference attenuation characteristic registered in advance in a storage unit 30. The plurality of filter coefficient sequences generated in this manner are provided to the filter 16. In the filter 16, the filter coefficient sequence is set for each observation point depth. As a result, the passband characteristic is dynamically changed as the observation point depth is increased.

In the preparation step, the plurality of filter coefficient sequences may be calculated in advance, and the filter coefficient sequences may be given to the filter 16 before the examination step. The configuration from the filter 16 to the image formation unit 20 functions in the examination step after the preparation step. However, this configuration may function in the preparation step. As will be described later, the plurality of reference attenuation characteristics may be registered in the storage unit 30.

An operation panel 32 is connected to the calculation controller 24. The operation panel 32 comprises a plurality of switches, a plurality of knobs, a trackball, a keyboard, and the like. In the embodiment, the operation panel 32 has a button 33 that is operated in tuning of the passband characteristic. The button 33 may be a virtual button displayed on the touch panel.

Figure 2:
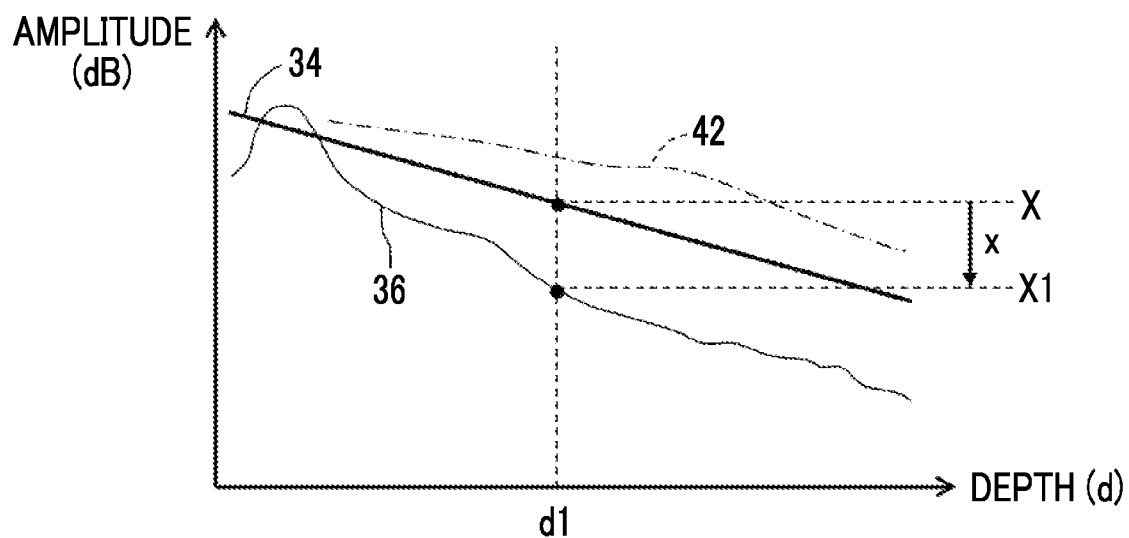
FIG. 2 is a diagram showing a reference attenuation characteristic and an actual measurement attenuation characteristic.

In FIG. 2, a reference attenuation characteristic 34 and an actual measurement attenuation characteristic 36 are shown. A horizontal axis is a depth axis, which indicates the observation point depth. A vertical axis indicates an amplitude of the reception signal. The ultrasound is attenuated in a process in which the ultrasound propagates through the living tissue. The reference attenuation characteristic 34 indicates a standard ultrasound attenuation characteristic. The actual ultrasound attenuation degree is changed in accordance with the examinee. For example, in a case of the examinee who has a large amount of fat, the attenuation of the ultrasound in the body of the examinee is relatively large. In a case of the examinee who has a small amount of fat, the attenuation of the ultrasound in the body of the examinee is relatively small.

Reference numeral 36 indicates the actual measurement attenuation characteristic. For example, the actual measurement attenuation characteristic can be acquired from one beam data corresponding to one ultrasound beam, or the actual measurement attenuation characteristic can be acquired from one reception frame data generated by the electronic scanning of the ultrasound beam. In the latter case, the data is integrated and accumulated, or averaged for each observation point depth.

For example, the reference attenuation characteristic 34 has an amplitude X at a depth d1, and the actual measurement attenuation characteristic 36 has an amplitude X1 at a depth d1. A difference (amplitude difference) between the amplitudes is x. The passband characteristic of the filter is changed in accordance with x. Such control is performed for each observation point depth. By the way, reference numeral 42 indicates another actual measurement attenuation characteristic.

The passband characteristic of the filter has the convex form (form convex upward) in a two-dimensional coordinate system defined by a frequency axis and a gain axis. The convex form can include a trapezoidal form, in addition to a Gaussian distribution form. The convex form has a width in the frequency axis direction at the constant gain. The constant gain is, for example, −30 dB with the peak (0 dB) as a reference.

In the embodiment, as will be described in detail with reference to FIGS. 4A to 4C, the peak position with respect to the width of the convex form is changed while the width of the convex form is fixed at each observation point depth. As a result, the passband characteristic is changed. More specifically, the peak position is changed to the low-frequency side or the high-frequency side while the upper limit and the lower limit of the width are fixed. As a result, the convex form is biased to the low-frequency side or the high-frequency side. The convex form may be deformed to the low-frequency side or the high-frequency side. By changing the peak position while the upper limit and the lower limit of the width are fixed, a problem that the texture of the ultrasound image is significantly changed and a user feels uncomfortable is less likely to occur.

Figure 3:
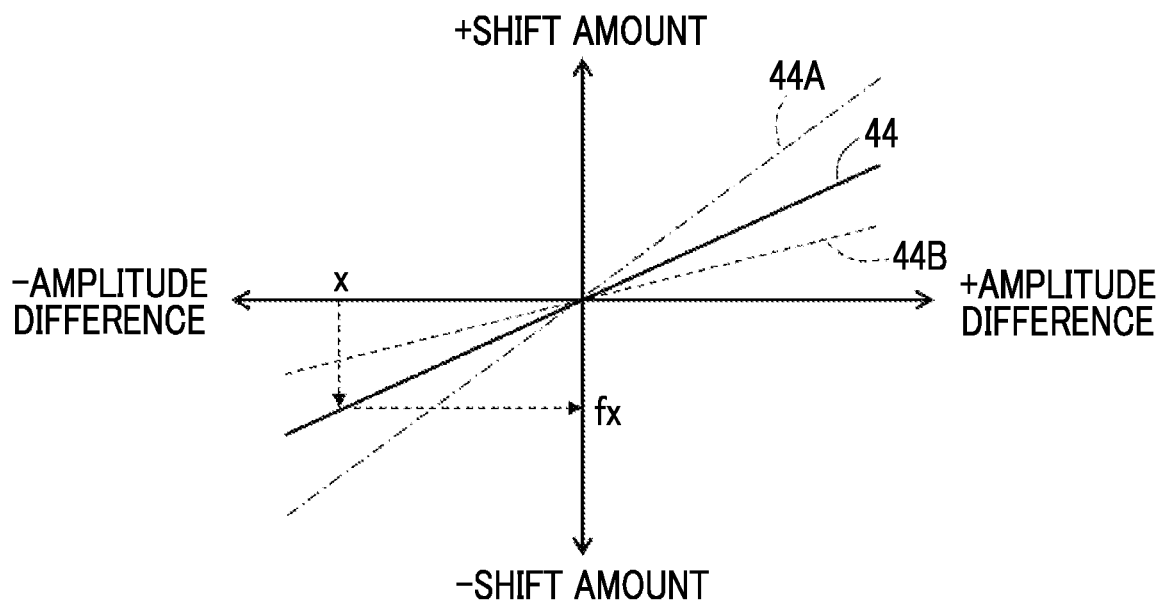
FIG. 3 is a diagram showing an example of a shift amount decision function.

FIG. 3 schematically shows a shift amount decision function. A horizontal axis indicates the amplitude difference (difference between the actual measurement attenuation characteristic and the reference attenuation characteristic), and a vertical axis indicates a shift amount of the peak position. For example, in a case in which the amplitude difference is x, a shift amount fx is decided in accordance with the shift amount decision function 44. The peak position of the convex form is changed in accordance with the shift amount fx.

Reference numeral 44A indicates another shift amount decision function, and reference numeral 44B indicates still another shift amount decision function. For example, the shift amount decision function to be used may be selected from among a plurality of shift amount decision functions in accordance with the observation point depth. In FIG. 3, a linear shift amount decision function is shown, but this is an example, and a non-linear shift amount decision function may be used.

Figure 4A:
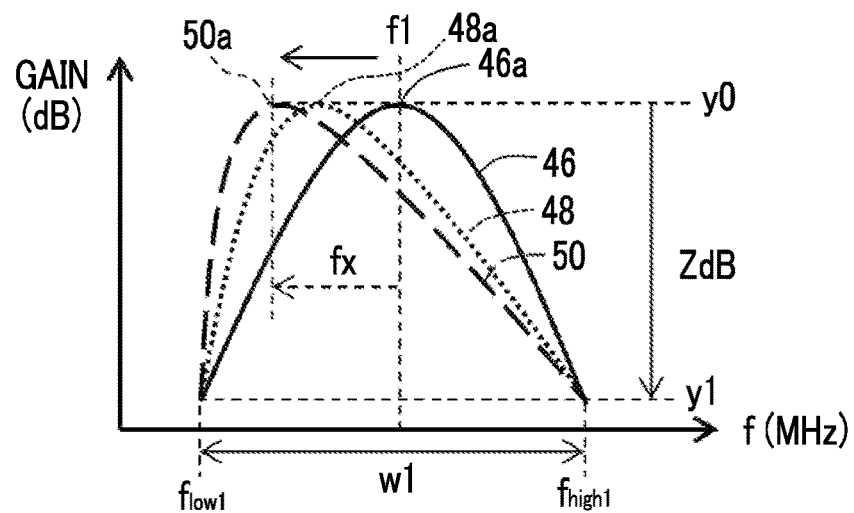
FIGS. 4A to 4C are diagrams showing a deformation in a convex form on a low-frequency side.
Figure 4B:
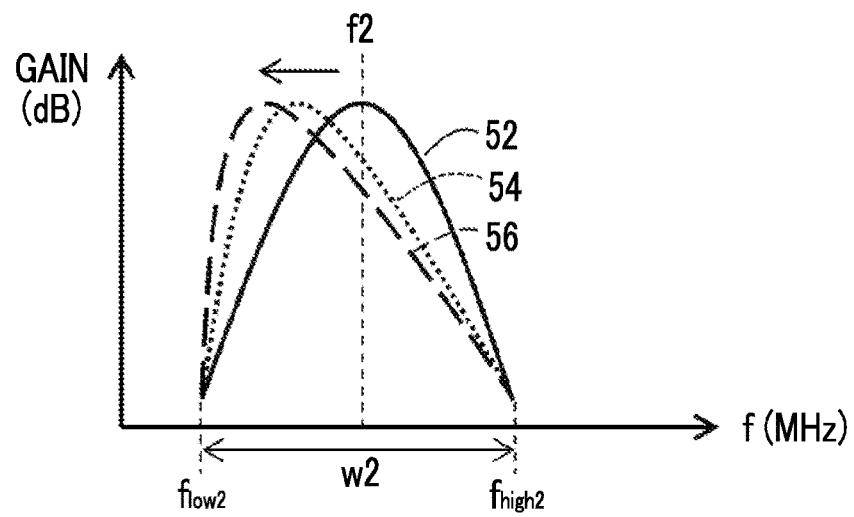
Figure 4C:
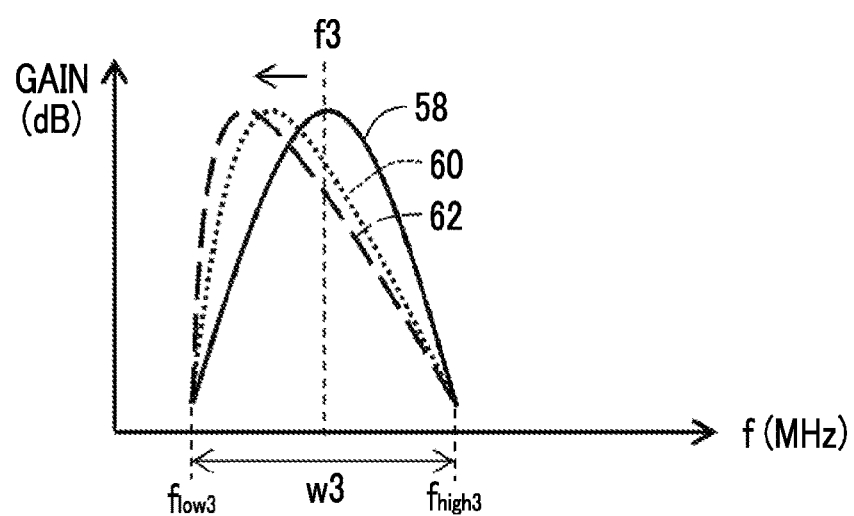

FIGS. 4A to 4C show change examples of the peak position. FIG. 4A shows a change example of the peak position at a relatively shallow depth position, FIG. 4B shows a change example of the peak position at an intermediate depth position, and FIG. 4C shows a change example of the peak position at a relatively deep depth position. Each of the change examples shows the change in the peak position on the low-frequency side.

A center frequency in a case in which the shift amount is zero is indicated by f1 at the relatively shallow depth position. In this case, a position of a peak 46a matches f1 on the frequency axis. As the shift amount is increased, the peak position is moved to the low-frequency side (see reference numerals 48a and 50a). The convex form indicating the passband characteristic is biased to the low-frequency side and is deformed as indicated by reference numerals 46, 48, and 50. For example, in a case in which the shift amount is fx, the convex form 50 is set as the passband characteristic. In this case, the peak position 50a is determined by f1−fx.

Even in a case in which the peak position is changed, a position and a size of a width w1 in the convex forms 46, 48, and 50 are maintained. That is, an upper limit $f_{high1}$ and a lower limit $f_{low1}$ of the width w1 are fixed. The width w1 is a width at a position at which the gain is lowered by −Z dB from the highest point (that is, the peak level) on the gain axis. −Z dB is, for example, −30 dBd. The gain of the peak level is indicated by y0, and the gain that is lowered by −Z dB from the peak level is indicated by y1. The amount of deformation in the convex form is increased as the peak position is changed.

The center frequency in a case in which the shift amount is zero is f2 at the intermediate depth position. As the shift amount is increased, the peak position is moved to the low-frequency side, whereby the convex form is biased to the low-frequency side (see reference numerals 52, 54, and 56). An upper limit $f_{high2}$ and a lower limit $f_{low2}$ are fixed, that is, a position and a size of a width w2 are fixed.

The center frequency in a case in which the shift amount is zero is indicated by f3 at the relatively deep depth position. As the shift amount is increased, the peak position is moved to the low-frequency side, whereby the convex form is biased to the low-frequency side (see reference numerals 58, 60, and 62). An upper limit $f_{high3}$ and a lower limit $f_{low3}$ are fixed, that is, a position and a size of a width w3 are fixed.

In the embodiment, the width is reduced as the observation point depth is increased. Specifically, the upper limit is changed as the width is changed, but the lower limit is fixed. Of course, the lower limit may be changed. It should be noted that all of the passband characteristics shown in FIGS. 4A to 4C are basically included in the passband characteristics of the ultrasound probe.

Figure 5:
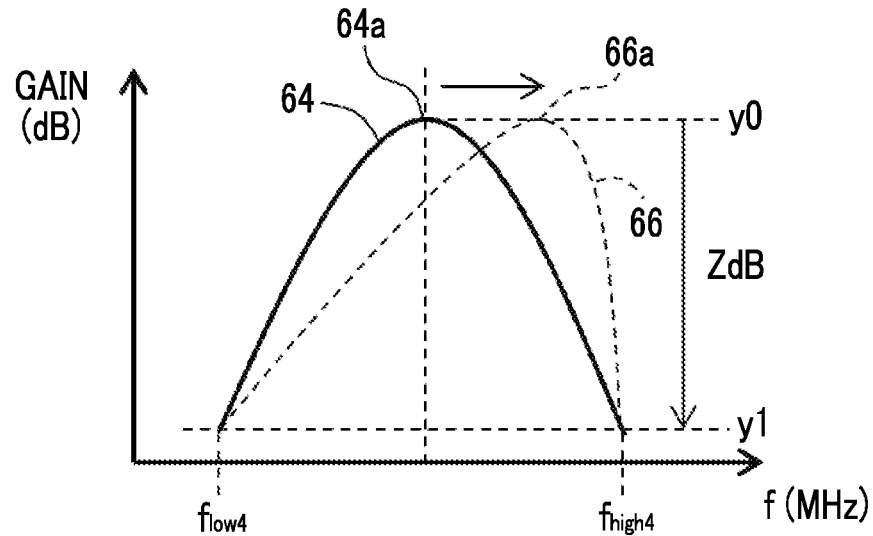
FIG. 5 is a diagram showing a deformation of a convex form on a high-frequency side.

FIG. 5 shows a change in the passband characteristic, that is, a change in the convex form in a case in which the peak position is changed to the high-frequency side at a certain depth position. The peak position is moved to the high-frequency side as a positive shift amount is increased (see reference numerals 64a and 66a). As a result, the convex form is biased (see reference numerals 64 and 66). The width at the constant gain is fixed. That is, an upper limit $f_{high4}$ and a lower limit $f_{low4}$ are fixed.

Figure 6:
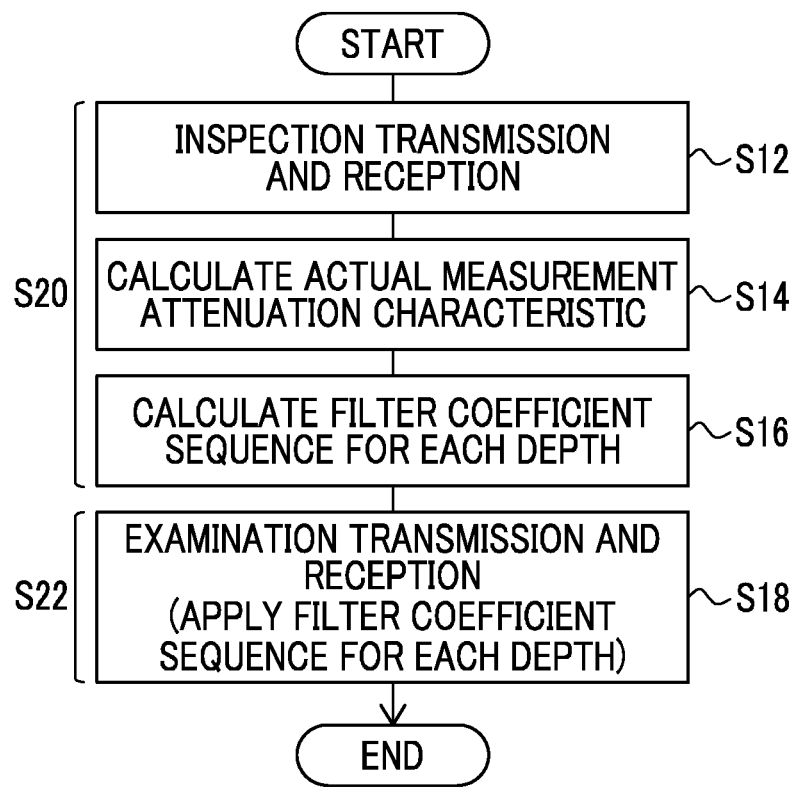
FIG. 6 is a diagram showing a preparation step and an examination step.

FIG. 6 shows an operation example of the ultrasound diagnostic apparatus according to the embodiment. The execution of the operation shown in FIG. 6 is started by operating a predetermined button on the operation panel. S20 indicates the preparation step, and S22 indicates the examination step after the preparation step.

In S12, the inspection transmission and reception are executed to actually measure the tissue property of the examinee. In this case, one ultrasound beam may be formed, the electronic scanning with the ultrasound beam may be performed, or a plane wave may be transmitted. In S14, the actual measurement attenuation characteristic is calculated and acquired based on the first reception signal obtained by the inspection transmission and reception. In S16, the amplitude difference is calculated for each observation point depth by comparing the actual measurement attenuation characteristic with the reference attenuation characteristic. In S18, the filter coefficient sequence is calculated for each observation point depth in order to realize the optimum passband characteristic. After the preparation step, in S18, the examination transmission and reception are executed. The second reception signal obtained as described above is processed by the band pass filter. The ultrasound image is formed and displayed based on the second reception signal output from the band pass filter. The filter coefficient sequence that is dynamically selected in accordance with the observation point depth is set in the band pass filter. As a result, a desired passband characteristic corresponding to the observation point depth is set.

The control of the passband characteristic according to the embodiment may be applied to a part of the depth direction instead of the entire depth direction. For example, the control of the passband characteristic according to the embodiment may be applied only to a region of interest. In this case, it is possible to obtain an advantage that the change in the texture in the depth direction can be suppressed in the region of interest.

Figure 7:
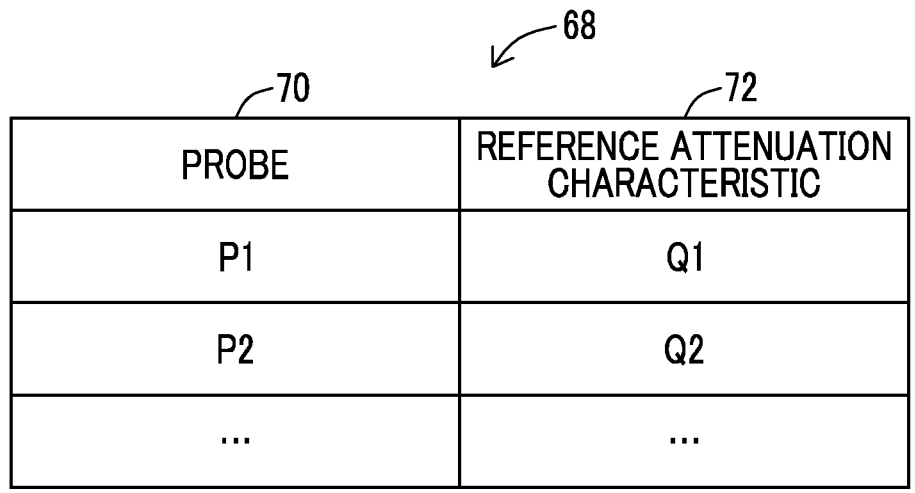
FIG. 7 is a diagram showing an example of a reference attenuation characteristic table.

FIG. 7 shows a reference attenuation characteristic table 68. The reference attenuation characteristic table 68 has a plurality of reference attenuation characteristics 72 corresponding to a plurality of probes 70. The reference attenuation characteristic corresponding to the used probe 70 is selectively used. The reference attenuation characteristic may be registered for each transmission center frequency. A single reference attenuation characteristic may be corrected in accordance with a situation, and the corrected reference attenuation characteristic may be used.

Figure 8:
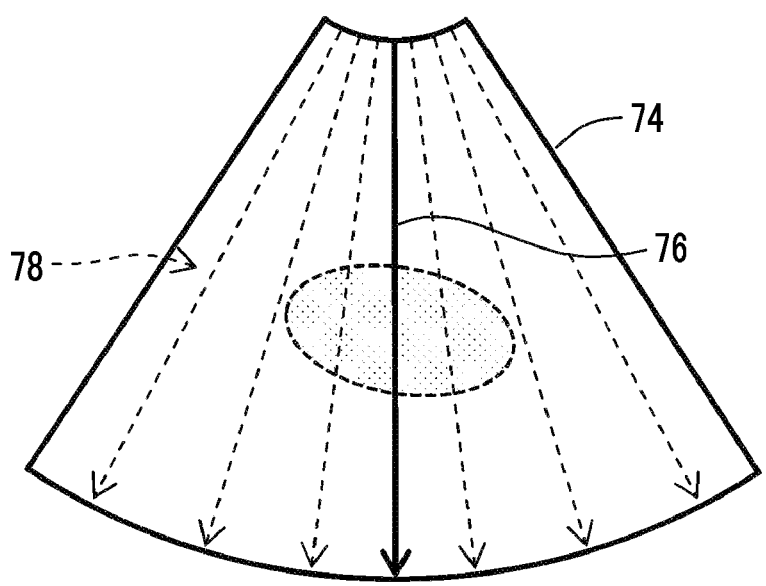
FIG. 8 is a diagram showing a transmission method in the preparation step.

In FIG. 8, the transmission and reception in the preparation step are shown. Reference numeral 74 indicates the beam scanning surface. For example, as indicated by reference numeral 76, a single ultrasound beam (transmission beam and reception beam) may be formed at a center position of the beam scanning surface 74. Alternatively, as indicated by reference numeral 78, a plurality of transmission beams may be sequentially or simultaneously formed in a plurality of directions. In this case, the electronic scanning with the ultrasound beam may be performed. Alternatively, the plane wave may be transmitted. In each case, a plurality of transmissions and receptions may be performed, and the plurality of reception signals obtained by the plurality of transmissions and receptions may be averaged. Information of a specific depth may be excluded in a case of acquiring the actual measurement attenuation characteristic. Thereafter, a missing portion may be supplemented by the interpolation of the actual measurement attenuation characteristic.

Figure 9:
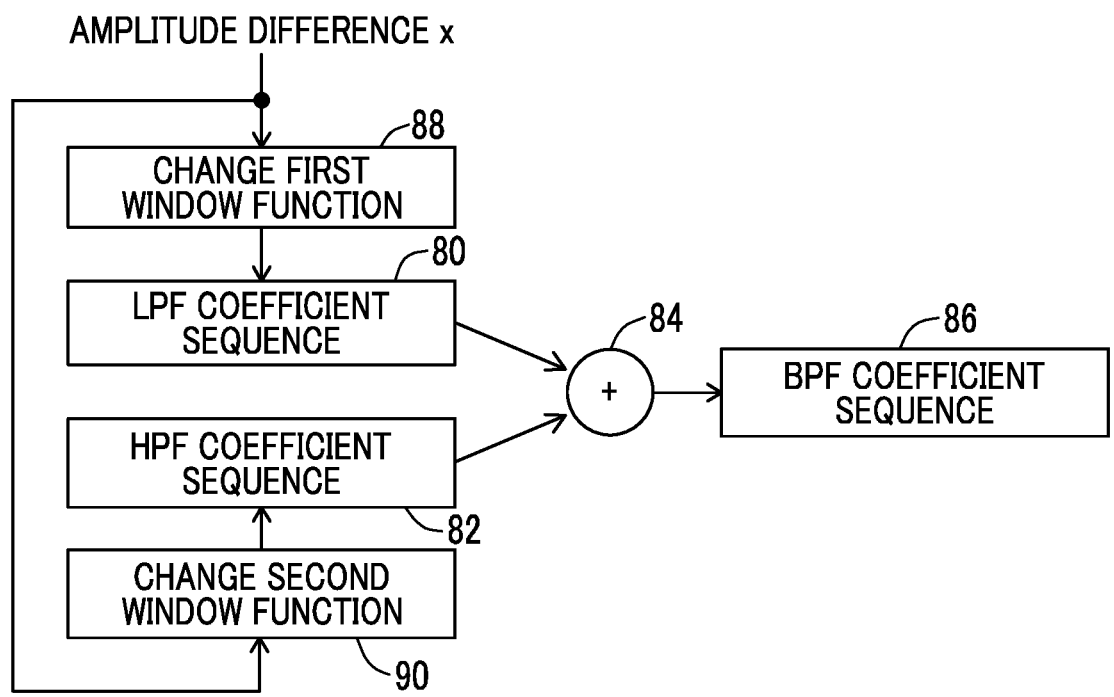
FIG. 9 is a diagram showing a generation method of a coefficient sequence.

FIG. 9 shows a generation method of a band pass filter (BPF) coefficient sequence 86. A combination (specifically, convolution) 84 of a low pass filter (LPF) coefficient sequence 80 and a high pass filter (HPF) coefficient sequence 82 generates the band pass filter (BPF) coefficient sequence 86. Before the combination 84, a first window function is multiplied by the LPF coefficient sequence 80. A second window function is multiplied by the HPF coefficient sequence 82.

In the embodiment, the first window function is changed in accordance with the amplitude difference x (see reference numeral 88), and the second window function is changed in accordance with the amplitude difference x (see reference numeral 90). As a result of the change in the first window function and the second window function, a desired passband characteristic of the BPF is realized. That is, the movement of the peak position, that is, the deformation in the convex form is realized by changing the first window function and the second window function.

In the embodiment described above, as shown in FIG. 3, the shift amount is decided from the amplitude difference in accordance with the shift amount decision function, but the shift amount may be decided from the amplitude difference by numerical calculation. In a case in which the convex form is a trapezoidal form and the top thereof has a spread in the frequency axis direction, the center of the top may be regarded as the peak.

What is claimed is:

1. An ultrasound diagnostic apparatus comprising:
   a transducer that transmits ultrasound to an inside of an examinee, receives a reflected wave from the inside of the examinee, and outputs a reception signal which is an electronic signal;
   a band pass filter through which the reception signal, which is an electronic signal and is output from the transducer, passes;
   a former that has a processor to form an ultrasound image based on the reception signal output from the band pass filter; and
   a controller that dynamically changes a passband characteristic of the band pass filter in accordance with an increase in an observation point depth in the examinee,
   wherein the passband characteristic of the band pass filter through which the electronic reception signal passes has a convex form, and the convex form has a peak as a highest point in a gain axis direction, and a width in a frequency axis direction, and the controller changes a peak position with respect to the width in accordance with the examinee at at least one observation point depth, and
   an upper limit and a lower limit of the width at the at least one observation point depth are substantially maintained in a case in which the peak position is changed with respect to the width.

2. The ultrasound diagnostic apparatus according to claim 1,
   wherein the width in the frequency axis direction is a width at a constant gain, the constant gain being determined with the peak as a reference.

3. The ultrasound diagnostic apparatus according to claim 1,
   wherein the convex form is deformed while being biased to a low-frequency side as the peak position is changed to the low-frequency side, and
   the convex form is deformed while being biased to a high-frequency side as the peak position is changed to the high-frequency side.

4. The ultrasound diagnostic apparatus according to claim 1,
   wherein the controller
      acquires an actual measurement attenuation characteristic based on the reception signal output from the transducer, and
      decides the peak position with respect to the width based on the actual measurement attenuation characteristic.

5. The ultrasound diagnostic apparatus according to claim 4,
   wherein the controller compares the actual measurement attenuation characteristic with a reference attenuation characteristic and decides the peak position with respect to the width based on a result of the comparison.

6. The ultrasound diagnostic apparatus according to claim 4,
   wherein the ultrasound diagnostic apparatus sequentially executes a preparation step and an examination step,
   in the preparation step, the actual measurement attenuation characteristic is acquired based on a first reception signal output from the transducer, and
   in the examination step, the passband characteristic of the band pass filter through which a second reception signal output from the transducer passes is changed based on the actual measurement attenuation characteristic.

* * * * *